United States Patent [19]

MacCollum et al.

[11] Patent Number: 4,904,265
[45] Date of Patent: Feb. 27, 1990

[54] CEMENTLESS ACETABULAR IMPLANT

[75] Inventors: Maureen A. MacCollum, Warsaw, Ind.; C. McCollister Evarts, Humelstown, Pa.; Richard R. Tarr, Warsaw, Ind.

[73] Assignee: Boehringer Mannheim Corporation, Indianapolis, Ind.

[21] Appl. No.: 243,479

[22] Filed: Sep. 9, 1988

[51] Int. Cl.$^4$ .............................................. A61F 2/34
[52] U.S. Cl. ...................................................... 623/22
[58] Field of Search .................... 623/16, 18, 19, 20, 623/22, 23

[56] References Cited

U.S. PATENT DOCUMENTS

| | | | |
|---|---|---|---|
| 3,840,904 | 10/1974 | Tronzo | 623/22 |
| 3,855,638 | 12/1974 | Pilliar | 623/16 |
| 3,874,003 | 4/1975 | Moser et al. | 623/18 |
| 3,882,550 | 5/1975 | Karpf et al. | 623/18 |
| 3,918,102 | 11/1975 | Eichler | 623/22 |
| 4,324,006 | 4/1982 | Charnley | 623/22 |
| 4,437,193 | 3/1984 | Oh | 623/22 |
| 4,623,352 | 11/1986 | Oh | 623/22 |
| 4,685,923 | 8/1987 | Mathys | 623/22 |
| 4,695,282 | 9/1987 | Forte et al. | 623/22 |
| 4,743,267 | 5/1988 | Tronzo | 623/22 |

FOREIGN PATENT DOCUMENTS

| | | | |
|---|---|---|---|
| 3346048 | 10/1985 | Fed. Rep. of Germany | 623/22 |
| 2117646 | 10/1983 | United Kingdom | 623/22 |

OTHER PUBLICATIONS

Park, J. B., Von Recum, A. F., Gratzick, G. E., "Pre-Coated Orthopedic Implants with Bone Cement", in *Biomaterials, Medical Devices and Artificial Organs,* 7 (1), pp. 41–53, 1979.
Miller, J., and Johnson, J. A., "Advances in Cementing Techniques in Total Hip Arthroplasty", in *The Art of Total Hip Arthroplasty,* Stillwell, William Thomas (ed.), 1987, pp. 277–280.
Brochure entitled "Universal Acetabular Cup System–Implant Options for Virtually Any Acetabular Reconstruction", pub. by DePuy, Warsaw, Indiana, Copyright 1987, 6 pages.
Wilson, J. M. and Scales, J. T., "Loosening of Total Hip Replacements with Cement Fixation–Clinical Findings and Laboratory Studies", in *Clinical Orthopaedics and Related Research,* No. 72, Sep.–Oct. 1970, pp. 145–160.

Primary Examiner—Richard J. Apley
Assistant Examiner—David J. Isabella
Attorney, Agent, or Firm—Perman & Green

[57] ABSTRACT

A cementless acetabular implant intended for use in instances of a bony defect in the pelvis at the acetabular cavity requiring substantial rebuilding of the acetabulum by use of bone graft material. It includes a substantially rigid metallic hemispherically shaped support cup for contiguous reception with the bone within the acetabular cavity. A flange extends outwardly from a peripheral rim of the support cup for supportive engagement on bone stock located beyond the acetabular cavity. The flange also serves to contain the bone graft material. The outer convex surface of the support cup is porous, as is a medial surface of the flange, to accept bone ingrowth. A bearing insert of low friction material for receiving the ball of a femoral prosthetic component is mounted in contiguous engagement with an inner surface of the support cup. Screws may be used to initially fix the support cup to the bone and a central apical hole provides visual confirmation during implantation that the support cup is completely seated into the acetabulum.

7 Claims, 3 Drawing Sheets

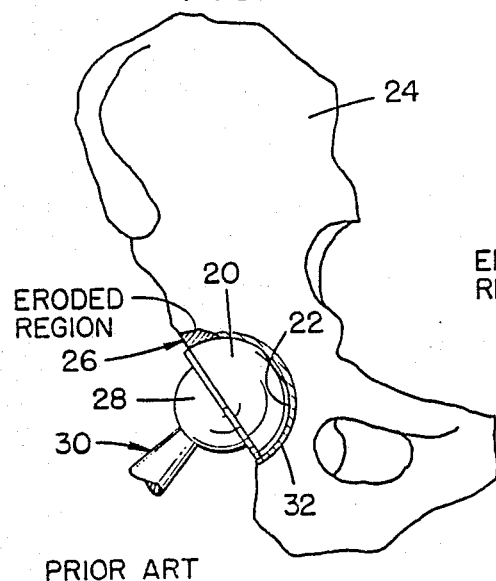
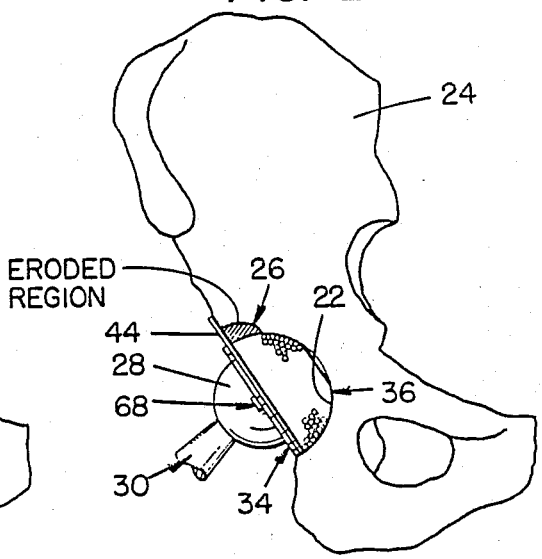
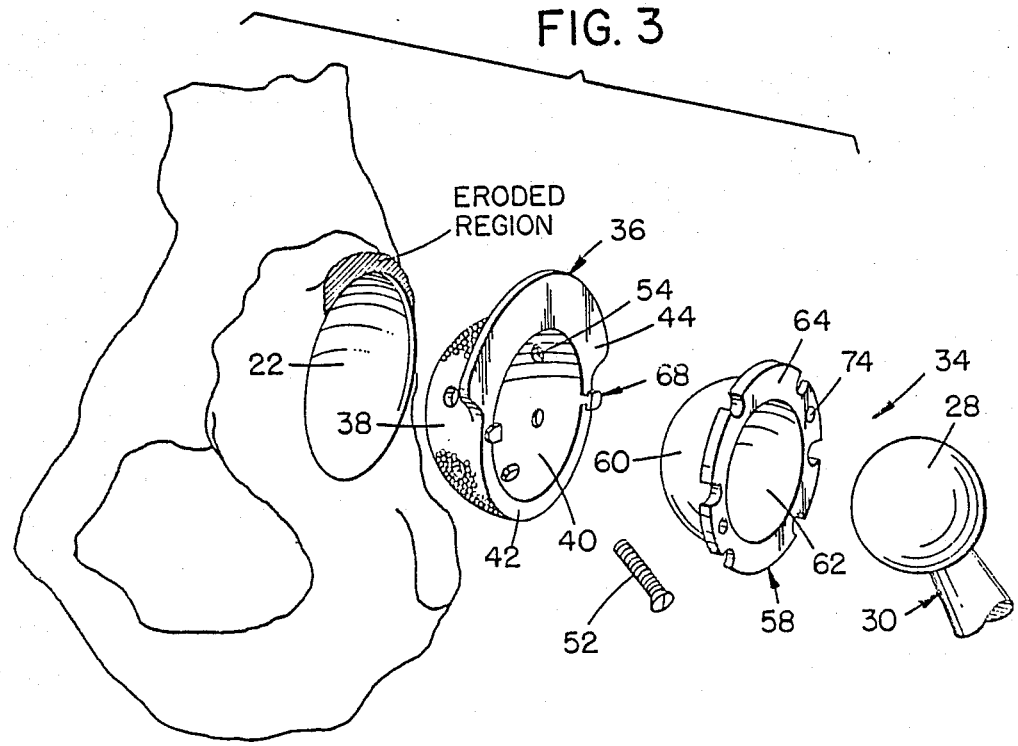

CEMENTLESS ACETABULAR IMPLANT

FIELD OF THE INVENTION

The present invention relates generally to artificial hip joints and, more particularly, to a cementless acetabular implant intended for use in instances of a bony defect in the pelvis at the acetabular cavity requiring substantial rebuilding thereof by use of bone graft material.

BACKGROUND OF THE INVENTION

A hip joint comprises a socket or acetabulum and a femoral head or ball received in the acetabulum. As such, the hip joint is a ball and socket joint which provides universal motion.

Various diseases, such as osteoarthritis, are known to attack the hip joint and, when this occurs, it may be necessary to utilize an appropriate hip joint prosthesis to replace the femoral head and the acetabulum. Replacement may also be necessary in other circumstances, such as in the instance of certain hip joint fractures.

Deterioration of the acetabulum requires that an acetabular cup be mounted in the acetbular cavity to provide a socket for receiving the prosthetic femoral head. If the medial wall of the acetabulum is sufficiently weakened, it has previously been found desirable to protect this wall with a protrusio shell or ring. A typical construction of a protrusio ring is disclosed in U.S. Pat. No. 4,623,352. In that instance, before implanting, a plastic acetabular cup is first interlocked with the protrusio ring, then the two components in unitary fashion are cemented into place on the acetabulum.

Another example of a protective implant for the acetabulum is disclosed in U.S. Pat. No. 3,918,102. In this instance, a generally annular shaped support member bears firmly against bone tissue surrounding the acetabular cavity. A spherical portion of the support member is configured for reception with the bone in the acetabular cavity but defines a substantially sized opening in its central regions. Bone cement is used to affix the support member and its spherical portion to the acetabulum. Subsequently, a hemispherical socket is inserted into the support member and is also affixed to the acetabulum through the central opening in the support member.

The use of acrylic cement for fixation of implants to bone was made popular by orthopedic pioneer Sir John Charnley and continues to be widely used. Although cement was fully accepted in the early years of total hip arthroplasty, its use is being subjected more and more to question. As early as 1970, loosening of hip joint components was recognized as a worrisome problem and, by the latter part of that decade, loosening had been identified as the most common complication in total hip arthroplasty. As related by Park et al in their paper entitled "Pre-Coated Orthopedic Implants with Bone Cement" published in the *Journal of Biomaterials, Medical Devices and Artificial Organs*, Vol. 7, No. 1 (1979) on page 42:

"Some problems can be attributed to the following intrinsic properties of the bone cement itself:
1. The monomer and additives are toxic.
2. The polymerization is exothermic and accompanied by a volumetric shrinkage.
3. The strength and stiffness are much lower than bone and implant.
4. Short working time and no recourse to correct mistakes (extremely hard to remove after cured, particularly from a long intramedullary site).
5. Abrasion particulate of cement may cause bone necrosis causing the loosening of implant."

Additional problems with cement have been reported by Miller and Johnson in their paper entitled: "Advances in Cementing Techniques In Total Hip Arthroplasty", being Chapter 19 in *The Art of Total Hip Arthroplasty* edited by William Thomas Stillwell, M.D., and published in 1987 by Grune and Stratton, Inc. In that paper, Miller and Johnson state that the exothermic character of polymerization of the acrylic cement suggests the possibility of bone injury and note on page 277 that "even Charnley postulated that thermal damage to the endosteal bone of the femur is to be expected." They further indicate that carcinogenesis has also been suggested although no clear evidence has emerged from clinical studies to support such a suggestion. Thus, it is clear that the use of acrylic cement for fixation of orthopedic implants is becoming more and more suspect, thereby inviting alternative constructions and procedures.

SUMMARY OF THE INVENTION

It was with knowledge of the state of the technology as just described that the present invention has been conceived and is now reduced to practice. To this end, a cementless acetabular implant is disclosed which is intended for use in instances of a bony defect in the pelvis at the acetabular cavity requiring substantial rebuilding of the acetabulum by use of bone graft material. It includes a substantially rigid metallic hemispherically shaped support cup for contiguous reception with the bone within the acetabular cavity. A flange extends outwardly from a peripheral rim of the support cup for supportive engagement on solid bone stock located beyond the acetabular cavity. The flange also serves to contain the bone graft material. The outer convex surface of the support cup is porous coated, as is a medial surface of the flange, to accept bone ingrowth. A bearing insert of low friction material for receiving the ball of a femoral prosthetic component is mounted in contiguous engagement with an inner surface of the support cup. Screws may be used to initially fix the support cup to the bone and a central apical hole may be employed to provide visual confirmation during implantation that the support cup is completely seated into the acetabulum. It is particularly noteworthy that the acetabular implant of the invention is provided with porous surfaces for accepting and encouraging bone ingrowth. Such a surface may be an inherent feature of the component itself, that is of the support cup, or it may be a coating such as that disclosed in U.S. Pat. No. 3,855,638, the disclosure of which is incorporated herein by reference.

A primary feature or benefit of the invention, then, resides in the provision of an acetabular implant of simplified construction which can be readily and securely mounted to a grossly deformed acetabulum without undue trauma to the underlying tissue. In optimum instances, the flange extends a sufficient distance to engage firm underlying bone at a location spaced from the acetabular cavity. This provides maximum stability to the implant during the healing period, and afterwards. In any event, the flange provides a structure for support and containment of the bone graft material used in the rebuilding of the acetabulum. Following implantation, bone ingrowth assures the permanent fixation of the implant which, therefore, is not subject to the loosening which often occurs to implants requiring the application of cement.

Other and further features, objects, advantages, and benefits of the invention will become apparent from the following description taken in conjunction with the following drawings. It is to be understood that both the foregoing general description and the following detailed description are exemplary and explanatory but are not restrictive of the invention. The accompanying drawings, which are incorporated in and constitute a part of this invention, illustrate some of the embodiments of the invention and, together with the description, serve to explain the principles of the invention in general terms.

BRIEF DESCRIPTION OF THE DRAWINGS

FIG. 1 is a front elevation view, certain parts being cut away and shown in section, illustrating a conventional hip joint implant;

FIG. 2 is a front elevation view, similar to FIG. 1, illustrating a hip joint implant embodying the present invention;

FIG. 3 is a perspective exploded view illustrating the components depicted in FIG. 2;

DETAILED DESCRIPTION OF THE PREFERRED EMBODIMENTS

Figure 4:
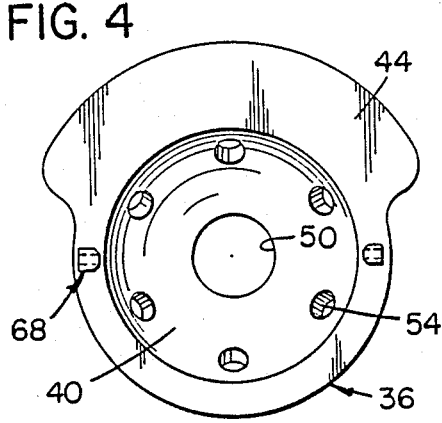
FIG. 4 is a lateral view of an acetabular cup embodying the invention.

Grossly deformed acetabula which are enlarged and eroded by reason of disease or a failed prosthesis (total hip implant) require major reconstruction of the bony structures of the pelvis. In instances in which large cavities exist or medial or superior migration of the socket has occurred, the surgical procedure of choice is to fill the defects with bone graft material and ream a new acetabular cavity, then hold the graft in place so it is anchored to good bone stock.

Turn now to the drawings and initially to FIG. 1 which depicts a known implant construction according to which a support cup 20 of conventional design has been implanted in the acetabular cavity 22 of a deformed pelvis 24. The deformation of the pelvis 24 is indicated as an eroded region 26 being, specifically, a deficiency in the acetabular cavity substantially reducing the area of support for the cup 20. In turn, the situation has an adverse affect on the ability of the support cup 20 to adequately support a ball or head 28 of a femoral component 30. FIG. 1 also is representative of an implant construction in which bone cement 32 is used for fixation of the support cup 20 to the acetabular cavity 22.

In contrast, turning now to FIGS. 2 and 3, an acetabular implant 34 of improved design is illustrated which is also intended for pivotal engagement by the head 28 of the femoral component 30.

In order to prepare the pelvis 24 for reception of the acetabular implant 34, it is necessary to ream the acetabular cavity with progressively larger reamers until the outer diameter measurement of a properly sized support cup 36 of novel design is approached. The proper size of the support cup 36 is preferably chosen by preoperative templating, although final size determination is performed during the reaming operation. The correct depth for reaming is influenced by the condition of the acetabulum, whether previous surgery had been performed, and the design of the support cup 36.

With respect to the condition of the acetabulum, it is always desirable to retain as much subchondral bone as possible. However, existing acetabular defects may require excision, as in the case of osteophytes or avascular sclerotic bone, and deficiencies may have to be remedied by bone grafting. Thus, by way of example, the eroded region 26 is to be built up with use of bone graft material which may autograft obtained from other locations in the patient's body, possibly from an excised femoral head in the event the procedure is a total hip arthroplasty being performed for the first time on the patient. Of course, the bone graft material may also be allograft or of a synthetic composition. In the event previous surgery was performed, and a cemented cup was used as indicated in FIG. 1, old cement must be completely removed prior to reaming for the new cup 36.

Figure 5:
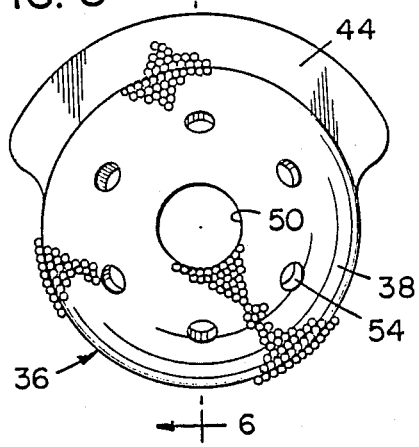
FIG. 5 is a medial view of the cup illustrated in FIG. 4.
Figure 6:
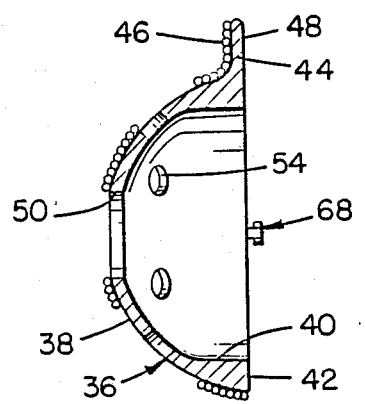
FIG. 6 is a cross section view taken generally along line 6—6 in FIG. 5.

Turning now to FIGS. 4–6 as well as to FIGS. 2 and 3, the support cup 36 is substantially rigid, being preferably composed of a suitable metal, such as titanium or titanium alloy. The support cup 36 is generally hemispherical in shape, although in fact, it may be greater than a hemisphere or less than a hemisphere, depending upon the particular shape and size of the acetabular cavity.

The support cup 36 has an outer convex surface 38 for contiguous reception with the bone within the acetabular cavity 22 and an inner concave surface 40. A peripheral rim 42 is located generally at an equator of the support cup and can be defined as a surface at the conjunction of the outer convex surface 38 and the inner concave surface 40. While the plane of the peripheral rim 42 may be flat, it may be curved about any desirable axis, or may even be undulated.

The support cup also includes a flange 44 lying generally in the plane of the peripheral rim 42 and extending outwardly from the outer convex surface 38. The flange 44 may subtend an angle generally in the range of 60° to 120°, although greater or lesser angles may be desired in specific instances. In any event, the flange 44 would subtend an angle of substantially less than 360° so as to avoid irritation of soft tissue by impingement. The flange 44 has a medial surface 46 which is an extension of and in communication with the outer convex surface 38 as well as a lateral surface 48 which is in communication with and an extension of the peripheral rim 42. Of particular emphasis for purposes of the present invention is the fact that the medial surface 46 and the outer convex surface 38 are porous for attachment by bone ingrowth to the bone within and surrounding the acetabular cavity 22. The porous surface may be an inherent feature of the support cup 36 and the flange 44 or it may be by way of an integral coating of the nature disclosed in U.S. Pat. No. 3,855,638 mentioned above.

A particularly desirable condition is illustrated in FIG. 2 in which the support cup 36 is mounted to the acetabular cavity 22 according to which the flange 44 extends beyond the acetabular cavity for supportive engagement on solid bone stock of the pelvis 24. In this instance, the flange 44 thus contains the bone graft material used in rebuilding the eroded region 26. In other less desirable situations in which the bony defect of the pelvis 24 is of a greater extent than that depicted, the flange 44 at least serves to contain most of the bone graft material and provides an extensive surface, namely medial surface 46, on which the bone ingrowth can occur with time.

As best seen in FIGS. 4-6, the support cup 36 may be provided with a central apical hole 50 distant from the peripheral rim 42. The purpose of the apical hole 50 is to provide confirmation to the surgeon during the implantation procedure that the support cup is completely seated into the acetabular cavity 22. Without such an expedient, considerable doubt remains as to whether the outer convex surface 38 is in a contiguous relationship with the bone forming the acetabular cavity 22. Failure to properly seat the support cup 36 in the acetabular cavity 22 may have substantial long term harmful effects painful to the patient and likely requiring a subsequent procedure to repair the defect. While the hole 50 is large enough to permit the type of observation just described, it is not so large that it has a deleterious effect on the strength of the support cup 36.

Initial attachment of the support cup may be achieved by means of a plurality of screws 52 which are received through associated screw holes 54 extending from the outer convex surface 38 to the inner concave surface 40 at peripherally spaced locations distant from the peripheral rim 42 and also spaced from the central apical hole 50. While, as stated, the screws 52 are used for initial attachment of the support cup 36 to the pelvis, long term fixation of the support cup 36 is dependent upon bone ingrowth which is permitted and encouraged by the porous outer convex surface 38 and the porous medial surface 46. In an alternative construction illustrated in FIGS. 7 and 8, the outermost regions of a modified support cup 36A may be provided with a plurality of circumferentially spaced screw holes 56 for reception therethrough of cooperating screws 52. Indeed, as illustrated in FIG. 7, the modified support cup 36A may simultaneously be provided with screw holes 54 and 56 to thereby provide the surgeon the option of using one set of screw holes or the other set, as he desires, during the surgical procedure.

Figure 7:
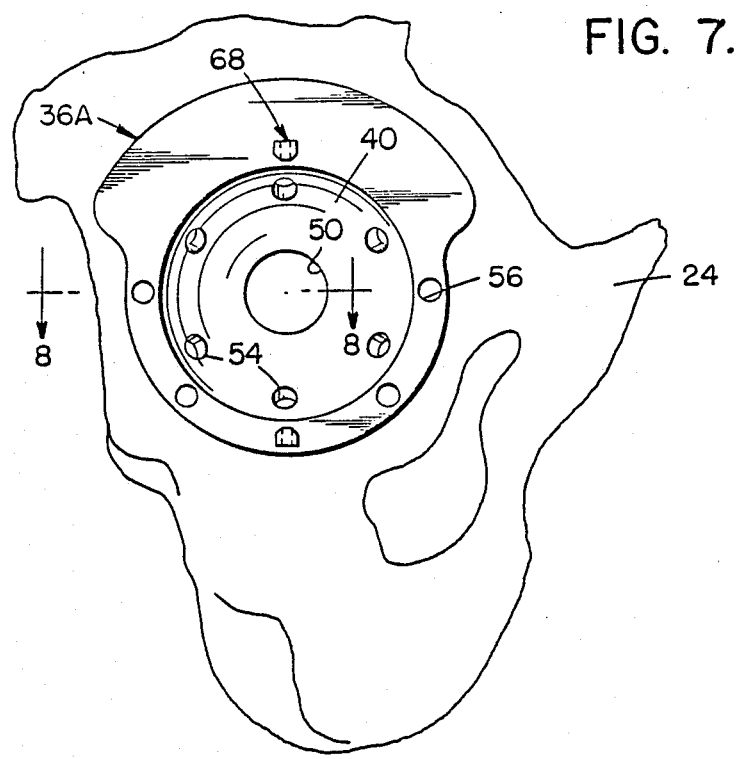
FIG. 7 is a lateral view depicting another embodiment of the acetabular cup of the invention.

While the flange 44 is illustrated as being oriented in a superior position in FIGS. 2, 3, and 7, it will be understood that the flange may be positioned in any orientation between a superior position and an inferior position depending upon the particular need pertaining at the time of a particular implant procedure.

In accordance with the invention, a bearing insert 58 of low friction material is adapted to be mounted on the support cup 36. The bearing insert may be of any suitable material including plastics, ceramics, or composite materials. In the event plastics are chosen, polyetheylene is a preferred material, although numerous other types of plastics may be suitable for purposes of the invention. Just as fixation of the support cup 36 to the pelvis 24 is to be achieved without the use of cement, so too, fixation of the bearing insert 58 to the support cup 36 is to be achieved without the use of cement. The bearing insert has an external convex surface 60 intended for contiguous engagement with the inner concave surface 40 of the support cup 36. Additionally, the bearing insert 58 has a spherical seat 62 for engageably receiving the head 28 of the femoral component 30 to enable universal pivotal movement of the femoral component relative to the pelvis 24.

Figure 9:
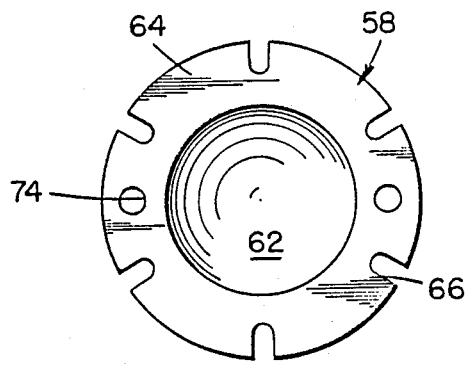
FIG. 9 is a lateral view of a bearing insert utilized as a component of the invention.
Figure 10:
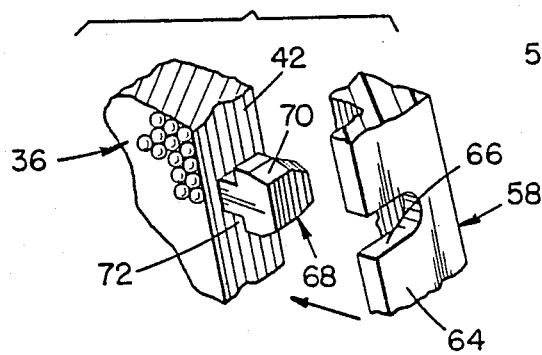
FIG. 10 is a detail perspective view illustrating a construction for fixedly mounting the bearing insert to the acetabular cup.
Figure 8:
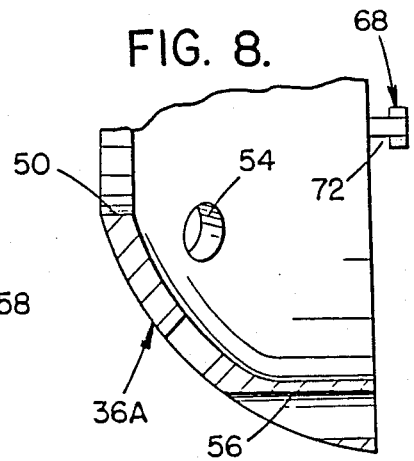
FIG. 8 is a detail cross section view taken generally along line 8—8 in FIG. 7.

One possible construction for mounting the bearing insert to the support cup is best illustrated in FIGS. 8-10. According to this construction, an annular lip 64 extends away from the spherical seat 62 and has a plurality of diametrically opposed U-shaped notches 66 formed at equally spaced circumferential locations. Each pair of notches 66 is dimensioned and positioned for receptive engagement by a pair of diametrically positioned holding tabs 68 formed on the rim 42 of the support cup 36 and extending in a direction away from the rim. Each holding tab 68 has a pair of outwardly directed cam surfaces 70 (see FIG. 10) and is undercut to form a pair of gripping surfaces 72 facing the rim 42 and being intermediate the rim and the cam surfaces. The width of each notch 66 is slightly smaller than that of its associated holding tab 68.

In actual practice, a tool (not shown) whose ends are received in a pair of diametrically opposed support apertures 74 (FIG. 9) positions the bearing insert 58 so that an appropriate pair of notches 66 is aligned with and positioned adjacent the holding tabs 68. Then, by use of an appropriate impactor tool (also not shown), each notch 66 is caused to ride up its associated cam surfaces 70, thereby becoming deformed, then snappingly returns to an original configuration so as to be held against removal by means of the gripping surfaces 72. As can be seen in FIG. 10, the depth of the holding tabs 68 between the rim 42 and its gripping surfaces 72 is substantially the same as the thickness of the annular lip 64 to assure that there is substantially no motion between the bearing insert 58 and the support cup 36 when the former has been mounted on the latter. While fixation of the bearing insert 58 on the support cup 36 is thereby achieved, a special tool (not illustrated) may be provided to readily remove the bearing insert 58 should that prove to be desirable.

While the preferred embodiments of the invention have been disclosed in detail, it should be understood by those skilled in the art that various modifications may be made to the illustrated embodiments without departing from the scope thereof as described in the specification and defined in the appended claims.

We claim:
1. A cementless acetabular implant for use in instances of a bony defect in the pelvis at the acetabular cavity requiring substantial rebuilding thereof by use of bone graft material comprising:
a substantially rigid metallic support cup, generally hemispherical in shape, having an outer convex surface for contiguous reception with the bone within the acetabular cavity, an inner concave surface, a peripheral planar rim being generally positioned at an equator of said support cup intermediate said outer convex surface and said inner concave surface, said support cup including a flange lying generally in the plane of said peripheral rim and extending outwardly from said outer convex surface for supportive engagement on bone stock located beyond the acetabular cavity and for containing the bone graft beneath said rim, said flange having a medial surface in communication with said outer convex surface and a lateral surface in communication with said peripheral rim, said outer convex surface and said medial surface being porous for attachment by bone ingrowth to the bone within and surrounding the acetabular cavity;

a bearing insert of low friction material adapted to be mounted on said support cup, said insert having an external convex surface contiguously engaged with said inner concave surface of said support cup, a spherical seat for engageably receiving a ball shaped member of a femoral prosthetic component to permit universal pivotal movement of the femoral component relative to the pelvis, and an annular lip intermediate said external convex surface and said spherical seat; and fixation means on said support cup including a pair of diametrically opposed holding tabs on said rim thereof extending in a direction away from said rim and spaced apart by a distance less than the breadth of said annular lip of said bearing insert, said holding tabs being undercut to form gripping surfaces and said bearing insert being deformable for reception on said support cup with said gripping surfaces overlying and engaging said annular lip for thereby fixedly mounting said bearing insert on said support cup and for positively preventing removal of said bearing insert from said support cup.

2. A cementless acetabular implant as set forth in claim 1 wherein said support cup has a central apical hole distant from said peripheral rim to provide visual confirmation during implantation that said support cup is completely seated into the acetabular cavity.

3. A cementless acetabular implant as set forth in claim 1 wherein said support cup has a plurality of screw holes extending from said outer convex surface to said inner concave surface at peripherally spaced locations distant from said peripheral rim for reception therethrough of screws for initial attachment to the pelvis.

4. A cementless acetabular implant as set forth in claim 1 wherein said support cup has a plurality of screw holes extending from said outer convex surface to said peripheral rim at peripherally spaced locations on said peripheral rim for reception therethrough of screws for initial attachment to the pelvis.

5. A cementless acetabular implant as set forth in claim 1 wherein said bearing insert is composed of material selected from the group consisting of plastics, ceramics, and composites.

6. A cementless acetabular implant as set forth in claim 5 wherein said plastic material is polyethylene.

7. A cementless acetabular implant for use in instances of a bony defect in the pelvis at the acetabular cavity requiring substantial rebuilding thereof by use of bone graft material comprising:

a substantially rigid metallic support cup, generally hemispherical in shape, having an outer convex surface for contiguous reception with the bone within the acetabular cavity, an inner concave surface, a peripheral planar rim being generally positioned at an equator of said support cup intermediate said outer convex surface and said inner concave surface, said support cup including a flange lying generally in the plane of said peripheral rim and extending outwardly from said outer convex surface for supportive engagement on bone stock located beyond the acetabular cavity and for containing the bone graft beneath said rim, said flange having a medial surface in communication with said outer convex surface and a lateral surface in communication with said peripheral rim, said outer convex surface and said medial surface being porous for attachment by bone ingrowth to the bone within and surrounding the acetabular cavity;

a bearing insert of low friction material adapted to be mounted on said support cup, said insert having an external convex surface contiguously engaged with said inner concave surface of said support cup and a spherical seat for engageably receiving a ball shaped member of a femoral prosthetic component to permit universal pivotal movement of the femoral component relative to the pelvis; and mutually engaging fixation means on said support cup and on said bearing insert for fixedly mounting said bearing insert on said support cup and for positively preventing removal of said bearing insert from said support cup;

wherein said mutually engaging fixation means includes:

an annular lip extending outwardly from the spherical seat of said bearing insert adapted for mating engagement with said peripheral rim when said bearing insert is mounted on said support cup, said annular lip having a plurality of pairs of circumferentially spaced, diametrically opposed, notches formed thereon;

a pair of diametrically opposed holding tabs on said support cup extending in a direction away from said rim, each holding tab having a pair of outwardly directed cam surfaces and being undercut to form gripping surfaces facing said rim and outwardly directed cam surfaces and being undercut to form gripping surfaces facing said rim and being located intermediate said rim and said cam surfaces;

each of the notches in said annular lip being dimensioned smaller than said associated tab and each pair of the notches being positioned to engage said pair of holding tabs when said annular lip is moved to a position proximate to said rim;

whereby with continued movement of said bearing insert toward said support cup, each notch is caused to ride up its associated said cam surfaces, thereby becoming deformed, then snappingly returning to an original configuration so as to be held against removal by means of said gripping surfaces.

* * * * *